(12) United States Patent
Halliday et al.

(10) Patent No.: US 6,488,953 B2
(45) Date of Patent: Dec. 3, 2002

(54) ORAL TRANSMUCOSAL DELIVERY

(75) Inventors: Janet Anne Halliday, Bo'ness (GB); Steven Robertson, Motherwell (GB)

(73) Assignee: Controlled Therapeutics (Scotland) Ltd., East Kilbride (GB)

( * ) Notice: Subject to any disclaimer, the term of this patent is extended or adjusted under 35 U.S.C. 154(b) by 0 days.

(21) Appl. No.: 09/872,759

(22) Filed: Jun. 1, 2001

(65) Prior Publication Data

US 2002/0037491 A1 Mar. 28, 2002

Related U.S. Application Data

(63) Continuation of application No. PCT/GB99/03985, filed on Nov. 29, 1999.

(30) Foreign Application Priority Data

Dec. 1, 1998 (GB) .............................. 9826192

(51) Int. Cl.$^7$ ................................ A61F 13/02
(52) U.S. Cl. ...................... 424/434; 424/435
(58) Field of Search ................. 424/434, 435

(56) References Cited

U.S. PATENT DOCUMENTS

| | | | | |
|---|---|---|---|---|
| 4,615,697 A | * | 10/1986 | Robinson | 604/890 |
| 5,113,860 A | * | 5/1992 | Mcquinn | 128/632 |
| 5,512,293 A | | 4/1996 | Landrau et al. | 424/449 |
| 5,571,528 A | | 11/1996 | Lee et al. | 424/440 |
| 5,624,667 A | | 4/1997 | El-Rashidy et al. | 424/435 |
| 5,639,469 A | * | 6/1997 | Benes et al. | 424/435 |
| 5,661,171 A | | 8/1997 | Acharya | 514/397 |
| 5,686,094 A | | 11/1997 | Acharya | 424/434 |
| 5,731,338 A | | 3/1998 | Acharya | 514/397 |
| 5,741,805 A | | 4/1998 | Acharya | 514/397 |

FOREIGN PATENT DOCUMENTS

| | | |
|---|---|---|
| GB | 2 047 094 A | 11/1980 |
| GB | 2 047 093 B | 12/1983 |
| GB | 2 047 094 B | 12/1983 |

OTHER PUBLICATIONS

Ch'ng, H.S. et al., "Bioadhesive Polymers as Platforms for Oral Controlled Drug Delivery II: Synthesis and Evaluation of Some Swelling, Water–Insoluble Bioadhesive Polymers", Journal of Pharmaceutical Sciences, vol. 74, No. 4: 399–405 (1985).

Park, H. et al., "Physico–Chemical Properties of Water Insoluble Polymers Important to Mucin/Epithelial Adhesion", Journal of Controlled Release, 2: 47–57 (1985).

Park, H. et al., "Mechanisms of Mucoadhesion of Poly (acrylic Acid) Hydrogels", Pharmaceutical Research, vol. 4, No. 6: 457–464 (1987).

Peppas, N.A., et al., "Hydrogels as mucoadhesive and bioadhesive materials: a review", Biomaterials 17: 1553–1561 (1983).

Tiwari, D. et al., "Evaluation of Polyoxyethylene Homopolymers for Buccal Bioadhesive Drug Delivery Device Formulations", PharmSci, Sep. 15, 1999; 1(3): 1–8, http://pharmsci.org/journal.

3M Pharmaceuticals, "3M Cydot Trunsmucosal Delivery System", Brochure: 1–8, 1995 (unconfirmed).

* cited by examiner

*Primary Examiner*—Carlos Azpuru
(74) *Attorney, Agent, or Firm*—Ropes & Gray

(57) ABSTRACT

An autoadhesive oral transmucosal delivery device contains a pharmaceutically active agent which is delivered via mucosal tissues in the mouth. The device comprises a dry hydrogel polymer which autoadheres to the moist mucosal surface for a time sufficient for release of active agent to occur before becoming detached.

19 Claims, 6 Drawing Sheets

Dissolution Profile of Apomorphine (17mg) from Polymer Strip (17mm x 5mm x 1mm)

Dissolution Profile of Apomorphine (4mg) from Polymer Disc (7mm x 1.2mm)

ORAL TRANSMUCOSAL DELIVERY

This application is a continuation of PCT/GB99/03985, filed Nov. 29, 1999, which claims priority to EGB 9826192.8 filed Dec. 1, 1998. The entire contents of the above reference patent applications are incorporated herein by reference.

The present invention relates to an autoadhesive oral transmucosal delivery device for delivering a pharmaceutically active agent via mucosal tissues in the mouth. The invention also relates to the use of a hydrogel body in preparation of a medicament for oral transmucosal delivery.

The transmucosal delivery of pharmaceutically active agents to a patient is known. In particular, the buccal region of the mouth in the upper gum and inside cheek region provides a barrier to delivery that is more permeable than the skin itself and tends to be less variable between individuals. The buccal mucosa also has a significantly lower depot effect than skin. The use of steroid mucoadhesive gels for the treatment of mouth ulcers is common, and is now a significant consumer market.

There are also technologies available which rely on the adhesion of a solid sustained delivery device to the mucosal membranes to allow sustained delivery of active agent. Such systems generally comprise an adhesive layer and a delivery matrix including the active agent, typically in the form of a small tablet or patch. In the Cydot (trademark) system the patch is non-degradable and must be removed after use. In the Theratech (trademark) system the tablet dissolves after a number of hours in situ. Advantages of transmucosal delivery are said to include rapid onset of drug delivery, sustained drug delivery levels and rapid decline of drug delivery at the end of the desired treatment time. The transmucosal route also delivers active agent directly into the system and avoids the first-pass through the liver metabolism process which is characteristic of oral delivery. The transmucosal membranes also appear to allow the passage of relatively high molecular weight drugs, including peptides.

Hydrogels are known sustained release delivery vehicles and a typical hydrogel having well documented pharmacological acceptability is disclosed in patent specifications GB2047093 and GB2047094 which describe cross-linked polyurethane materials having the ability to swell and absorb several times their own weight of water. The hydrogel polymer has been used as a pessary to deliver dinoprostone (a prostaglandin) to the cervix to ripen it prior to the induction of labour and is available under the trademarks Propess and Cervidil. The pessary is enclosed in a net pouch and usually remains in place for up to 24 hours.

The use of the hydrogel polymer for localised application for the treatment of maladies of the mouth has been disclosed in passing in the GB patent specifications mentioned above.

The immobilisation of transmucosal delivery devices in the buccal region is clearly desirable in order to prevent the device being accidentally swallowed by the patient. However, mucosal tissues have a high moisture content and it is correspondingly difficult to adhere solid devices to them in an effective manner. Moreover, any suitable adhesive must not only be effective but also pharmacologically acceptable, and the presence of a further component imposes undesirable complexities on the development of a suitable product.

The present invention is based on the surprising discovery of autoadhesive properties of the hydrogel to moist mucosal surfaces, allowing the device to remain in place over a time which is sufficiently extended to allow effective delivery of active agent.

In particular, the present invention provides an autoadhesive oral transmucosal delivery device which comprises:
 a body formed of a hydrogel capable of absorbing water to achieve a water-content whereat the device autoadheres to an oral mucosal surface;
 the hydrogel body comprising a pharmaceutically active agent which is released while the body is adhered to the mucosal surface.

The term "autoadhesive" in the present specification is taken to mean that the device itself adheres to the mucosal tissue by virtue of its own properties and without the need to employ any other adhesive material.

The invention also extends to the use of the hydrogel in an autoadhesive medicament for oral transmucosal delivery of active agent.

The hydrogel body as supplied will usually contain little or no water (e.g. less than 1 or 2 wt %) and will absorb water from the surroundings after administration. It is found that autoadhesion occurs at hydrogel water contents below 50% by weight, particularly less than 45% and especially less than 35% by weight. It is found that there is also generally a lower limit above which autoadhesion occurs of around 25% by weight. Autoadhesion typically requires a water content in the range 35 to 45% by weight. Generally, hydrogel polymer will be chosen such that the water uptake is sufficient to allow the device to firmly adhere to the mucosal membranes in less than 15 minutes (e.g. in 10 to 15 minutes). During this time, the patient may need to hold the device in place using his cheek muscles, and so this period should generally speaking not be longer than 10 to 15 minutes. Thereafter, the device should remain in place until the active agent has been substantially released. Generally, the device should remain adhered whilst it absorbs further water for a period of at least one hour, particularly at least 2 hours and preferably at least 4 hours. A preferred adherence period is in the range 2–3 hours before the device becomes detached. At this point, the patient knows that the treatment is complete and can spit out the spent device.

Generally, the hydrogel is a polyurethane hydrogel of the type disclosed in patent specifications GB2047093 and GB2047094. These patent specifications disclose cross-linked polyurethane hydrogels. Typically, the polyurethane is prepared from a long chain polyethylene glycol (e.g. PEG 2000, 4000, 6000 and 8,000 which has been extensively dried), a triol (for example hexanetriol) as cross-linking agent and a diisocyanate (such as dicyclohexyl isocyanate). The mixture is cured at elevated temperatures in a mould.

Other polymers such as polyhydroxyethylmethacrylates, polyvinylpyrrolidones and celluloses may be used provided they show the required autoadhesion properties.

The delivery device is generally in the form of a conformable unit, which is flexible enough (particularly when swollen) to be accommodated within the buccal cavity in intimate contact with the mucosal membrane. Preferred shapes include sheets, discs, ovals, kidney shapes, strips and cylinders. Generally, the smallest dimension is in the range 5–15 mm and the longest dimension in the range 10–25 mm. Preferred thicknesses are in the range 0.5–5 mm, especially 0.5 to 2.5 mm and particularly 1–2.5 mm.

Generally, the hydrogel is loaded with active agent by soaking the hydrogel in a solution of active agent of required concentration for a time sufficient for absorption to occur, followed by drying the hydrogel down to the required water content. Uptake of active agent may be improved by the use of low molecular weight cosolutes such as sodium chloride, potassium chloride, sodium saccharin and benzoic acid.

The objective of the device of the invention is to provide a controlled release of the active agent to the mucosal membrane during its period of adhesion. Preferably, the release rate is substantially constant through this period. The active agent may be absorbed systemically or may exert a local action on adjacent tissue structures.

If necessary, penetration enhancers, as known in the art, may be employed to assist the rate of transmucosal delivery, depending on the nature of the active agent, for example its lipophilic or hydrophilic characteristics, size and molecular weight. Generally, the more lipophilic the compound, the better the absorption. The nonionised form of the active agent appears to be best for absorption. The pH of the buccal tissue mucosa is around 6.8 and both acidic and basic active agents are suitable candidates. In view of the rapid and effective delivery through mucosal tissues, penetration enhancers may not be required. Such penetration enhancers are known from topical application to skin tissue which constitutes a more significant barrier to absorption. Weak acids and some detergents have been used as penetration enhancers.

The release properties of the hydrogel may be modified by applying a coating thereto. Poorly soluble drugs which would not be released satisfactorily from the hydrogel may be included in a coating.

In principal, the device of the present invention is applicable to the delivery of a wide variety of pharmaceutically active agents. Specific classes of active agent include abortifacients, hypnotics, sedatives, tranquilisers, anti-pyretics, anti-inflammatory agents, anti-histamines, anti-tussives, anticonvulsants, muscle relaxants, anti-tumour agents (for example those for the treatment of malignant neoplasia), local anaesthetics, anti-Parkinson agents, topical or dermatological agents, diuretics (for example those containing potassium, such as potassium iodide), preparations other than those containing prostaglandins for the treatment of mental illness (for example preparations containing lithium for use in the treatment of manic depression), anti-spasmodics, anti-ulcer agents, preparations containing various substances for the treatment of infection by pathogens including anti-fungal agents (for example metronidazole), anti-parasitic agents and other anti-microbials, anti-malarials, cardiovascular agents, preparations containing hormones (for example androgenic, estrogenic and progestational hormones, notably steroids such as oestradiol), sympathomimetic agents, hypoglycaemic agents, contraceptives, nutritional agents, peptides (for example insulin), preparations containing enzymes of various types of activity (for example chymotrypsin), preparations containing analgesics (for example aspirin), and agents with many other types of action including nematocides and other agents of veterinary application. Mixtures of active agents may be incorporated into the hydrogel.

The delivery device is particularly suited to the delivery of apomorphine, fentanyl and local anti-infective agents.

Active agents which require inconvenient intravenous administration due to poor oral bioavailability are particular candidates for delivery via the oral mucosal tissues. This delivery route offers a number of potential advantages:

rapid absorption and onset of action, bypass of first-pass liver metabolism, improved bioavailability for certain drugs, potential to minimise side effects by spitting the device out, delivery of peptides (which are normally degraded in the gastrointestinal tract), avoidance of gastric emptying factor effect on the rate and extent of absorption of the active agent, avoidance of affects associated with the presence of food in the stomach, and suitability for patients who do not like swallowing tablets or who are incapable of doing so.

Embodiments of the present invention will now be described by way of example only in the following figures and examples. The figures show the following:

Figure 7:
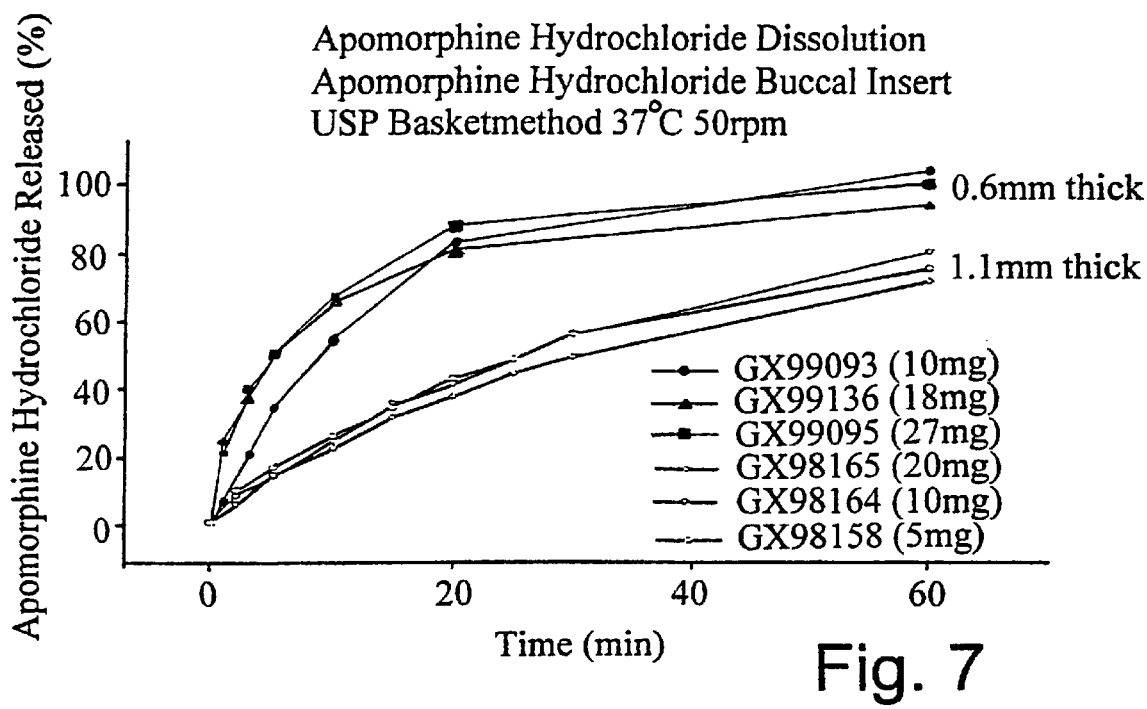
Figure 8:
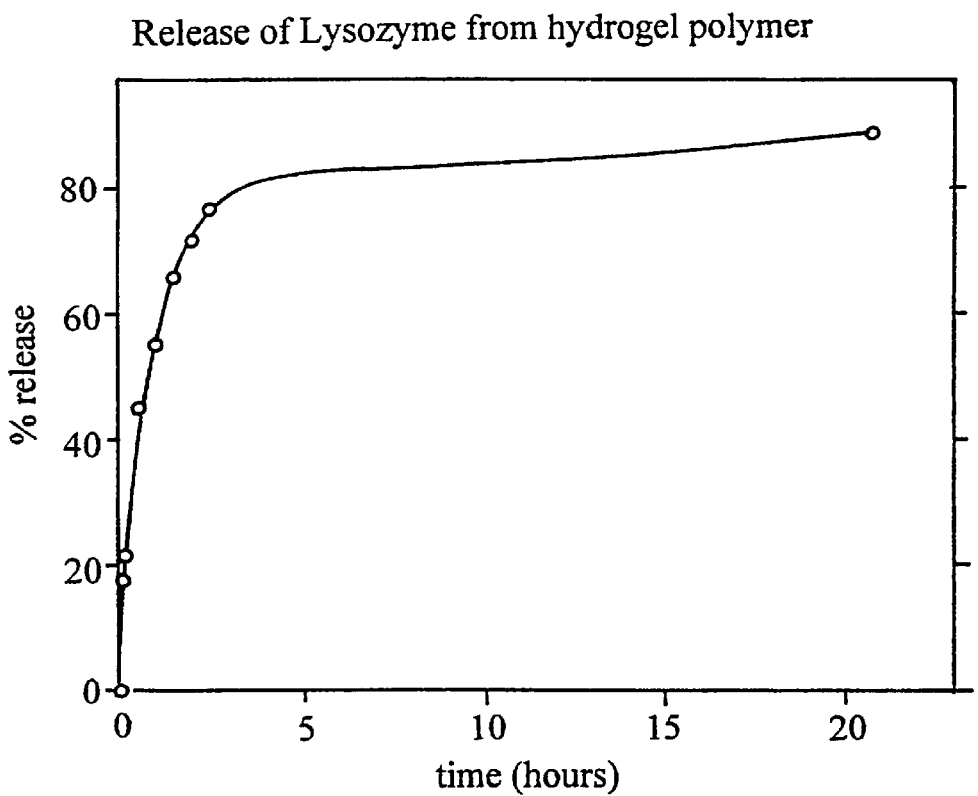
Figure 9:
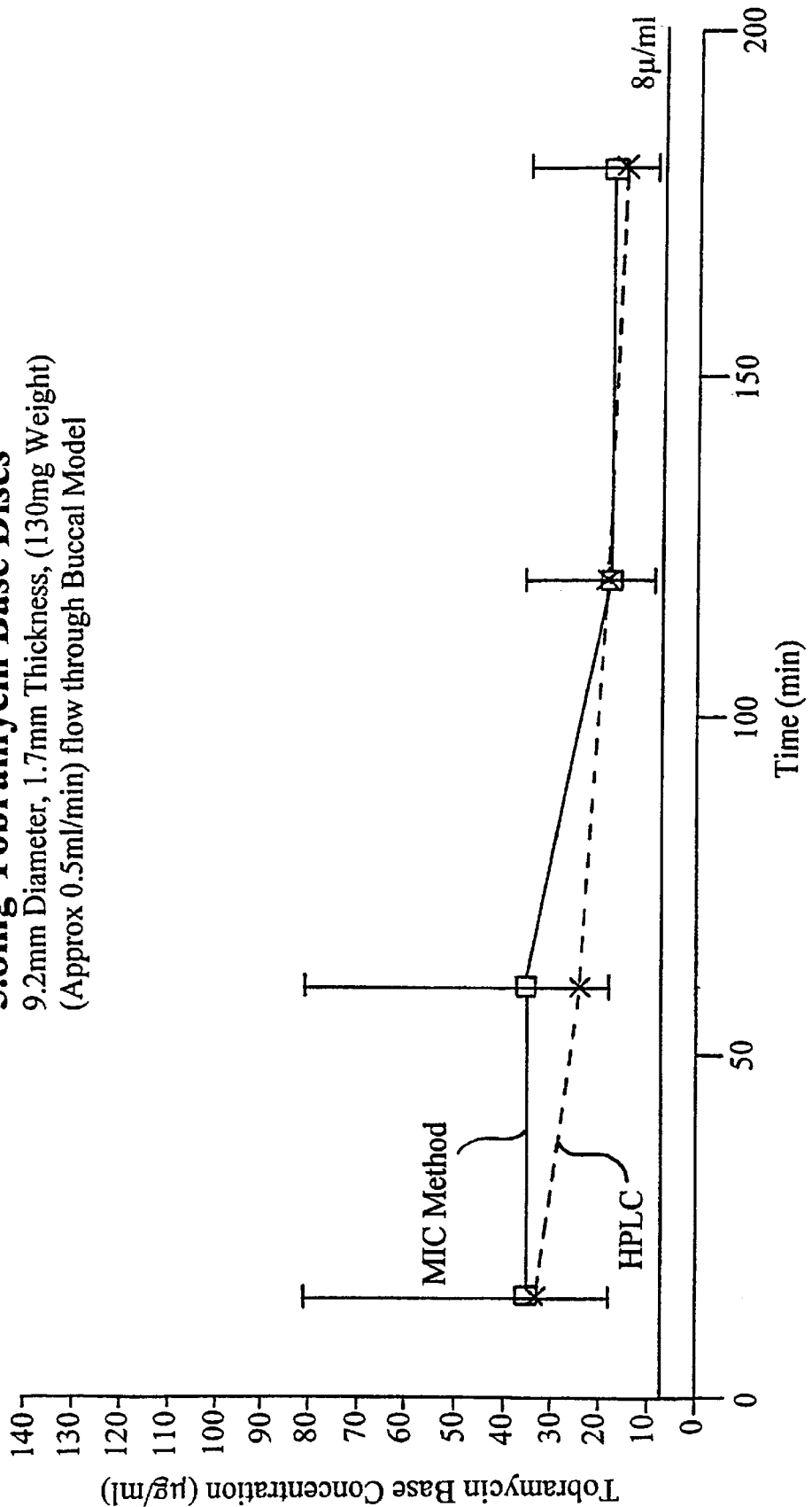
Figure 10:
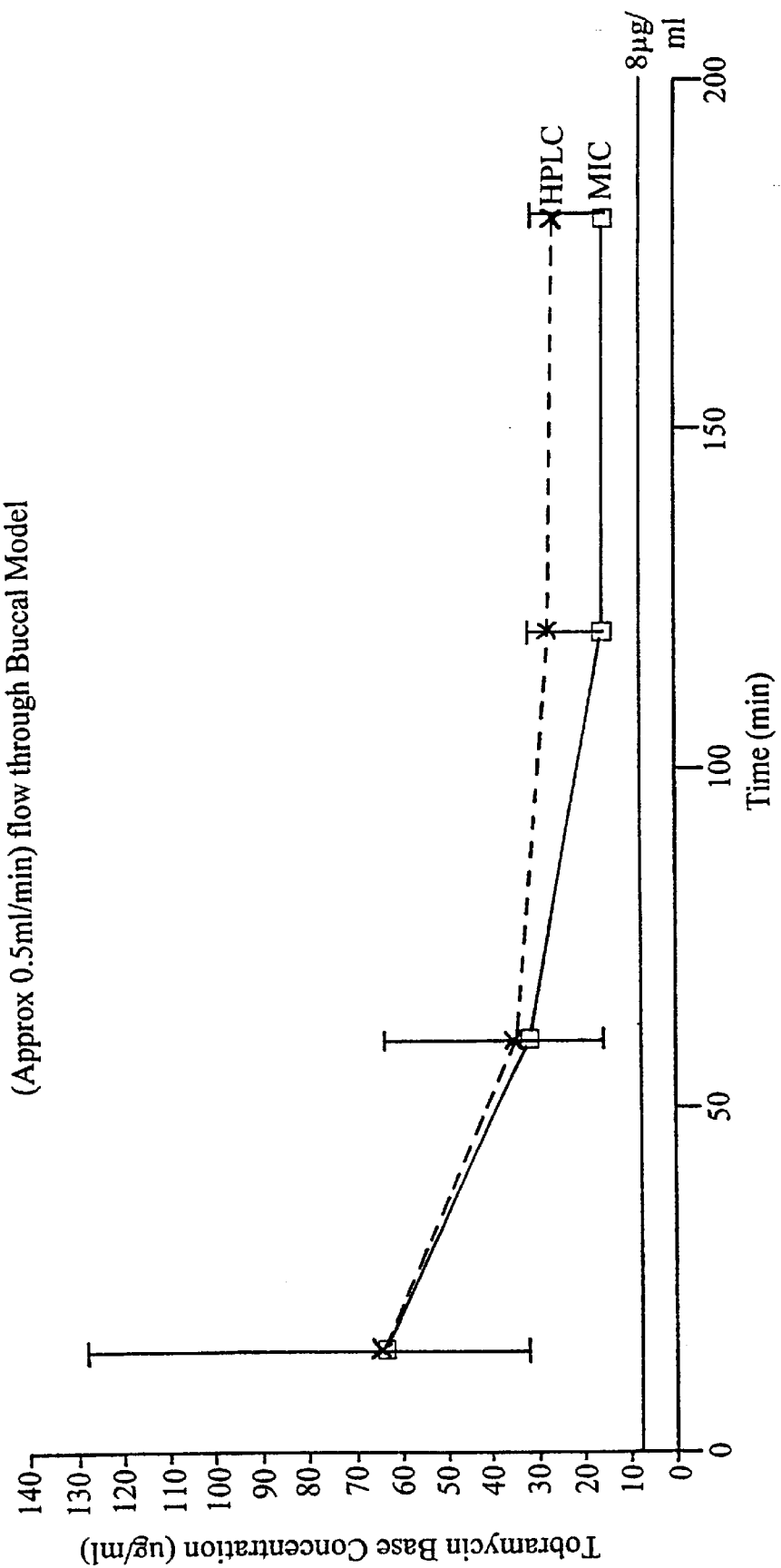

FIG. 7 compares the in-vitro dissolution rates of apomorphine from devices of different thickness;

FIG. 8 shows the in-vitro dissolution profile of the peptide lysozyme;

FIGS. 9 and 10 show dissolution profiles of tobramycin from a delivery device in the form of a disk.

The following examples will now be described.

EXAMPLE 1

Preparation of the hydrogel

The polymer is generally prepared following the methods set out in patent specifications GB2047093 and GB2047094. Briefly, the polymer is prepared by melting polyethylene glycol, adding hexanetriol in which ferric chloride is dissolved and then adding dicyclohexylisocyanate. The mixture is then cured at 95° C. in a mould. The stoichiometric ratio of the components is calculated depending on the molecular weight of the polyethyleneglycol.

EXAMPLE 2

Equilibrium Solvent Uptake in-vivo (Swelling/ESU)

The solvent uptake of the polymer was found to be much slower when the polymer was swollen in-vivo compared to in-vitro.

$$ESU = \frac{\text{Weight of swollen polymer} - \text{Weight of dry polymer}}{\text{Weight of dry polymer}} \times 100$$

(a) Trials

Figure 1:
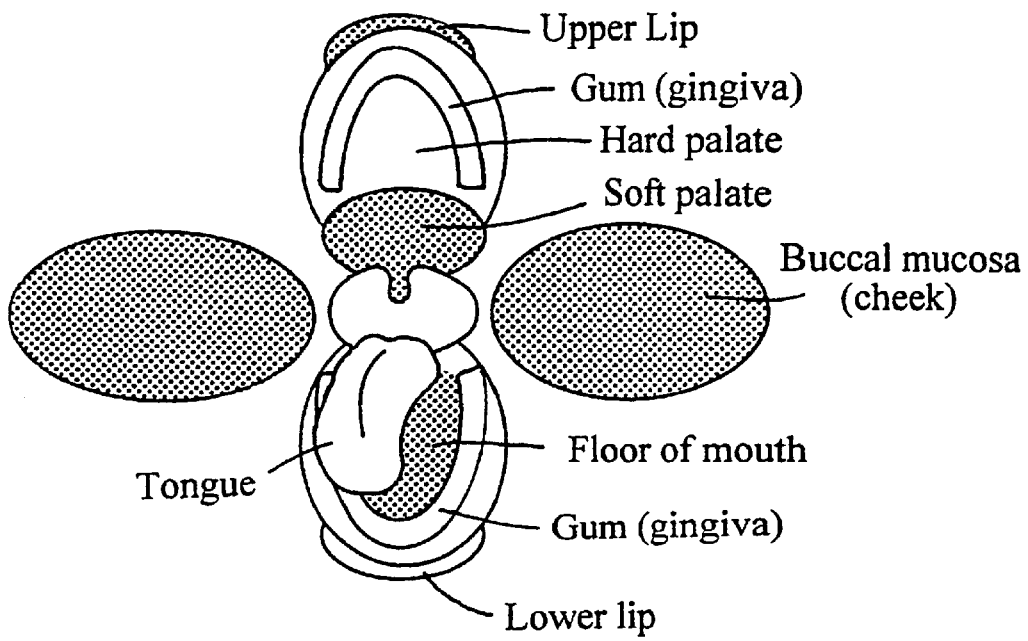
FIG. 1 shows schematically the location of the buccal mucosa.
Figure 2:
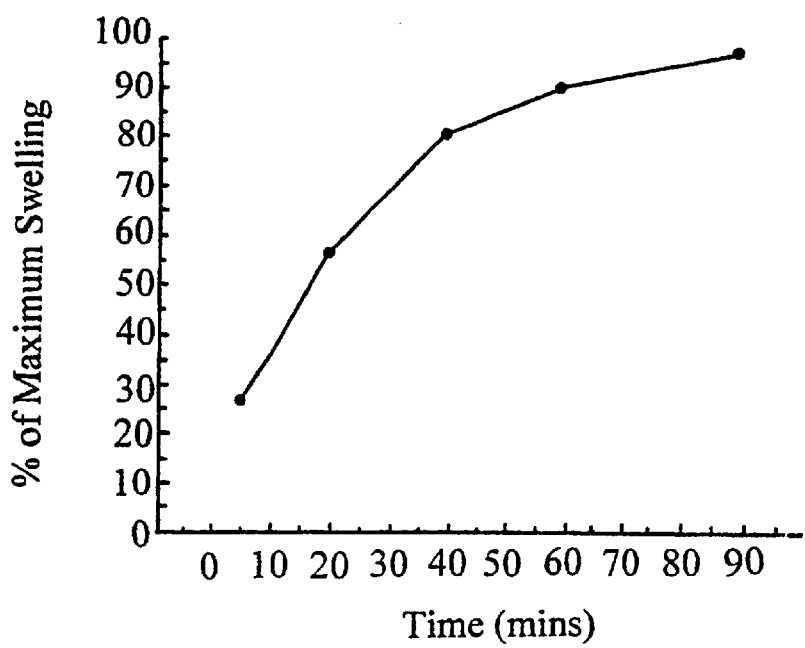
FIG. 2 shows in vitro swelling of hydrogel polymer disks.
Figure 3:
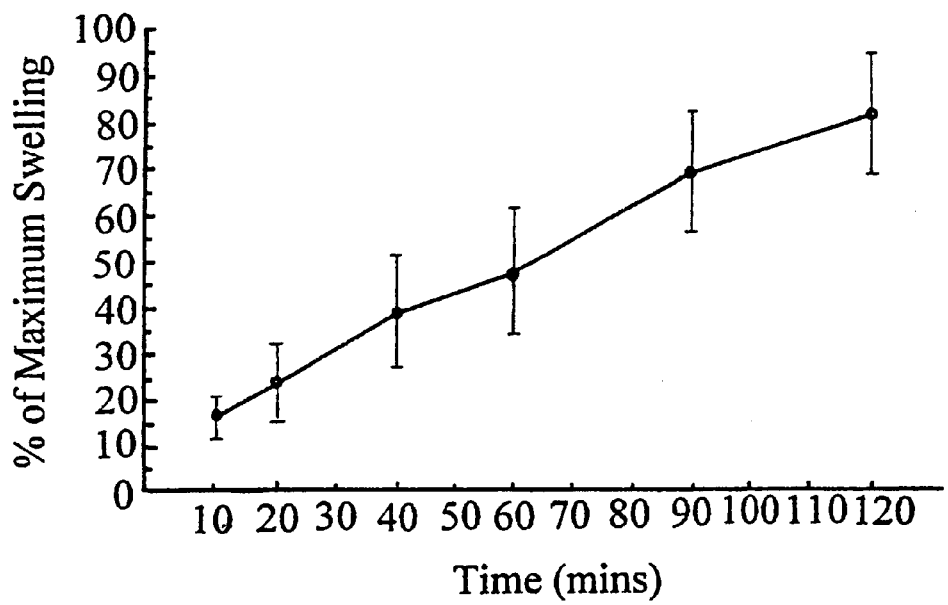
FIG. 3 shows in vivo swelling of polymer disks.

The results of a trial group of subjects to whom hydrogel delivery devices were administered are set out in the Tables 1 and 2 and FIGS. 2 and 3. When placed on the gingival mucosa the polymer was slightly uncomfortable initially in some instances, but this disappeared after a brief period of time.

TABLE 1

ESU: Polymer Composition: PEG 4000, 1.5 mm Thickness Rectangular Shapes (GX96010B)

| Time (mins) | In-Vivo Swelling (%) (n = 4) | Water Content (%) | Comments |
| --- | --- | --- | --- |
| 20 | 42 | 25 | Discomfort Reported |
| 40 | 73 | 37 | Discomfort Reported |
| 60 | 99 | 45 | No Discomfort Reported |
| 80 | 118 | 51 | No Discomfort Reported |
| 100 | 135 | 56 | No Discomfort Reported |
| 120 | 146 | 60 | No Discomfort Reported |

The "In-Vivo Swelling" is defined as:

$$\frac{\text{Weight of polymer removed from mouth} - \text{Weight of dry polymer}}{\text{Weight of dry polymer}} \times 100$$

TABLE 2

ESU: Polymer Composition: PEG 8000, 1.2 mm Thickness 7 mm Discs (GX97001)

| Time (mins) | In-Vitro ESU % | In-Vivo ESU (%) (n = 5) | Comments |
|---|---|---|---|
| 5 | 91 | — | |
| 10 | 145 | 43 | |
| 20 | 207 | 62 | |
| | 231 | | |
| 40 | 249 | 101 | |
| 60 | 253 | 124 | Polymer was difficult to remove from mucosal surface (n = 2) |
| 320 | 256 | — | | n = number of different people in the trial group.

These data suggest that polymer becomes firmly attached to the mucosal surfaces when it contains between 37 and 45% moisture (depending on polymer and size and shape of dosage form. The polymer patch is loosely attached about 10 minutes after placing on the buccal mucosa.

The comfort of the delivery system is dependent on the size and shape when dry and when swollen. The thickness and pliability of the unit are also important. Drug release is also affected by the shape of the polymer unit.

Figure 4:
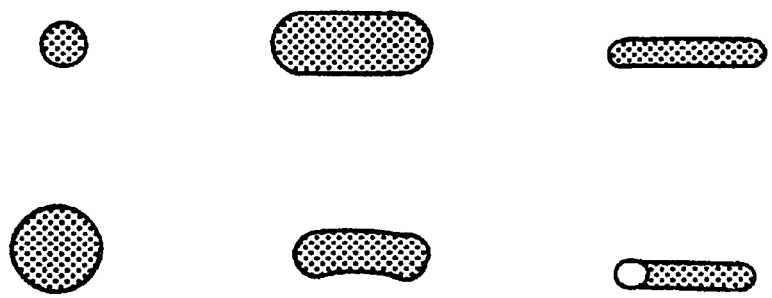
FIG. 4 shows possible shapes for the delivery device of the invention.

A range of shapes have been prepared and these are shown in FIG. 4. From left to right these comprise:

Disk (diameter 7 mm, thickness 1.2 mm)
Strip (length 15 mm, width 10 mm, thickness 1.5 mm)
Strip (length 17 mm, width 5 mm, thickness 1 mm)
Disk (diameter 13 mm, thickness 1.5 mm)
Lozenge (length 15 mm, width 10 mm, thickness 1.5 mm)
Cylinder (length 15 mm, diameter 3 mm)

(b) Comfort Trials (in vivo)

Further trials were carried out to assess the comfort and acceptability of various configurations of buccal hydrogel polymer device and to assess their swelling capacity. Twelve subjects (10 females and 2 males) of age range 20 to 55 years were recruited. Three configurations of buccal device were employed viz:

S1=10 mm diameter disc 1.43 mm thick
S2=13 mm diameter disc 1.46 mm thick
S3=lozenge (10 mm×14 mm) 1.7 mm thick The subjects had pre-insertion and post-insertion oral examinations and then pre-weighed delivery devices were placed on the buccal mucosa against the gingival margin. The inserts were kept in place for up to three hours, the subjects refraining from eating, drinking and smoking. Every 30 minutes, each subject scored the comfort, adherence and saliva production of the inserted delivery device. On removal from the subjects, the delivery devices were re-weighed. The results are given in Table 3A. Seven subjects stated a preference for delivery device S1, two preferred S2 and one preferred S3.

TABLE 3A

| | in-vivo results | | |
|---|---|---|---|
| | Shape 1 (10 mm disc) | Shape 2 (13 mm disc) | Shape 3 (lozenge) |
| Time Insitu (hr/min) | | | |
| Mean | 3:04 | 2:59 | 2:59 |
| Range | 2:56–3:10 | 2:33–3:07 | 2:33–3:09 |
| Comfort Rating (recorded every 30 min over 3 hrs) | | | |
| Very comfortable | 9 | 5 | 1 |
| Comfortable | 49 | 32 | 49 |
| Uncomfortable | 13 | 26 | 16 |
| Very Uncomfortable | 1 | 6 | 5 |
| Adhered Well (recorded every 30 min over 3 hrs) | 6 | 7 | 7 |
| Did Not Adhere Well (recorded every 30 min over 3 hrs) | 6 | 5 | 5 |
| Saliva Production (recorded every 30 min over 3 hrs) | | | |
| Unchanged | | | |
| Increased | 6 | 5 | 4 |
| Decreased | 2 | 1 | 0 |
| Increased & Decreased | 2 | 4 | 6 |
| | 2 | 2 | 2 |
| Adverse Reactions | 3 | 5 | 8 |
| Swelling (%) | | | |
| Mean | 206.1 | 187.6 | 205.4 |
| RSD | 16.2 | 25.1 | 15.1 |
| *Range | 167.7–250 | 158.9–238.5 | 144.7–245.4 |

(*S1 132% and S2 70.4% excluded from range only)

(c) Further Comfort Trials (in vivo)

In-vivo data (see later) suggested that a thinner polymer configuration was desirable. Therefore, a second comfort study was carried out to assess the comfort and acceptability of two 0.6 mm thick configurations of the buccal hydrogel device. Ten subjects (five female and five males) were recruited. The two configurations examined were:-

S4=9 mm wide×23 mm in length
S5=7.5 mm wide×28 mm in length

The subjects placed the pre-weighed delivery devices on the buccal mucosa against the gingival margin. The subjects were not permitted to eat or smoke but drinking was allowed, the quantity and type of liquid consumed was recorded. Every 30 minutes the subjects recorded comfort, adherence and saliva production. On removal of the insert, the delivery device was re-weighed and the ESU calculated. The results are given in Table 3B. Three subjects stated a preference for delivery device S4 and seven for device S5.

TABLE 3B

| | SHAPE 4 | | SHAPE 5 | |
|---|---|---|---|---|
| SUBJECT NO | ESU (%) | Proportion of Scores. Comfortable or Very Comfortable | ESU (%) | Proportion of Scores. Comfortable or Very Comfortable |
| 1 | 269 | 0% | 230 | 33% |
| 2 | 251 | 50% | 257 | 100% |
| 3 | 205 | 50% | 259 | 100% |
| 4 | 298 | 0% | 265 | 100% |
| 5 | 268 | 100% | — | 100% |
| 6 | 264 | 28% | 266 | 71% |

TABLE 3B-continued

| | SHAPE 4 | | SHAPE 5 | |
|---|---|---|---|---|
| SUBJECT NO | ESU (%) | Proportion of Scores. Comfortable or Very Comfortable | ESU (%) | Proportion of Scores. Comfortable or Very Comfortable |
| 7 | 200 | 33% | 266 | 100% |
| 8 | 269 | 86% | 255 | 100% |
| 9 | 262 | 100% | 274 | 100% |
| 10 | 268 | 100% | 248 | 86% |
| mean | 255 | — | 258 | — |
| overall proportion | — | 66% | — | 92% |
| preferred shape | 3 | — | 7 | — |

EXAMPLE 3

In-Vitro Model of Adhesion

Mucoadhesion occurs via two mechanisms

Water absorption giving intimate contact

Chain entanglement and formation of bonds (usually hydrogen bonds)

The first happens fairly quickly whilst the second takes longer to establish. Samples of hydrogel polymer were evaluated, using Carbobol 934P (non-hydrogel) and polyethylene oxide as positive controls. The latter tend to dissolve when swollen.

Tensile Testing

The technique used was based on that described by Mortazavi, S. A. and Smart, J. D., J.Contr Rel.31 (1994) 207 –212 and Smart, J. D., and Johnson, M. E., Eur.J Pharm-.Sci.4 Suppl. (1996)S65.

Polymer discs, circa 5 mm diameter, were tested as received. As positive controls Carbopol 934P (BF Goodrich) and polyethylene oxide (mw 4,000 KDa,Sigma) were compressed into 50 mg discs using 1 tonne force for 5 seconds.

The conclusion was that the hydrogel polymer was weakly adhesive compared to the non-hydrogel controls, the adhesion was comparable in strength to the commercially available products Adcortyl in Orabase and Buccastem. These are also weakly adhesive when examined by this method, but it has been shown that only a small adhesive force is required to retain a dosage form within the buccal cavity (Smart, J, Int J Pharm. 73(1991) 69–74). These experiments are being repeated and other models examined to further explore the nature of the adhesion observed in-vivo.

EXAMPLE 4

Drug Delivery (a)Centrally Acting Agonists

The improved delivery of drugs to the systemic circulation benefits drugs which may be acting in areas difficult to reach following oral delivery such as the central nervous system. The polymer was examined for delivery of apomorphine and fentanyl.

i) Apomorphine

Apomorphine is not well absorbed following oral administration and may cause yawning, nausea and vomiting. Bioavailability from the oral route is unpredictable.

Figure 5:
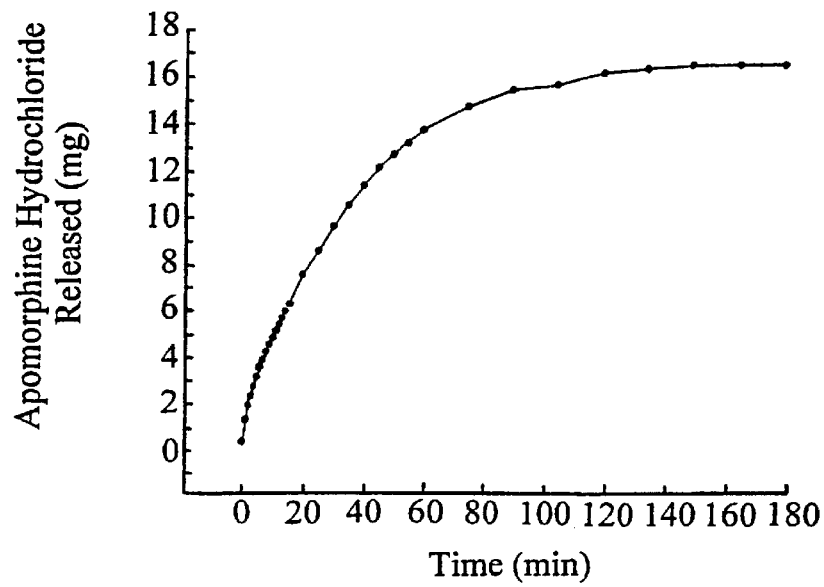
FIG. 5 shows the dissolution profile of apomorphine from a delivery device in strip form.

Parkinson's Disease:

Apomorphine is administered by intermittent and continuous sub-cutaneous injection for the treatment of the off periods of refractory Parkinson's disease. Although the injection is rapid and effective it is unpleasant and inconvenient to administer frequently in a 16 hr a day. Sufficient apomorphine was incorporated into the hydrogel polymer to expect to achieve, by buccal administration, the plasma levels required for effective therapy. The in-vitro release profile is shown in FIG. 5. The in-vitro release profile was determined by placing the units in 900 ml of deionised degassed water. Samples were taken at various intervals and analysed using U.V. spectoscopy at 272 nm.

Figure 6:
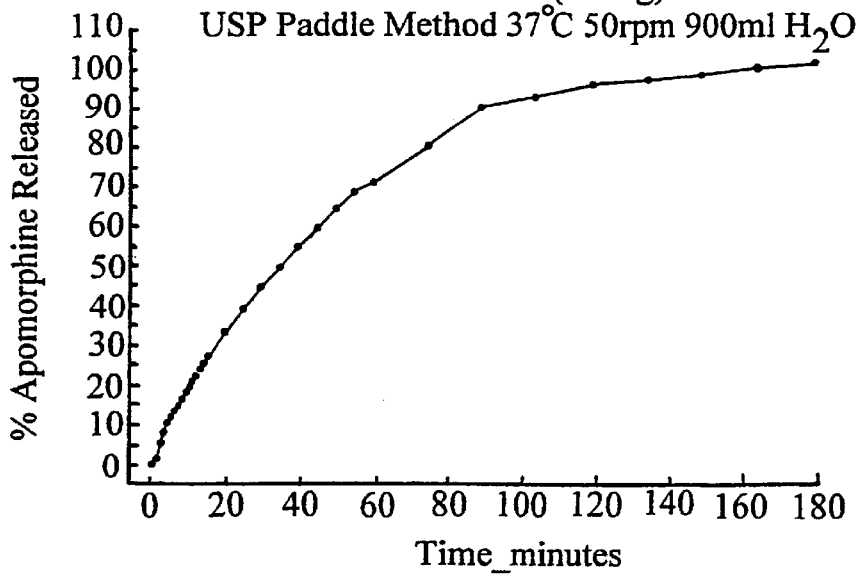
FIG. 6 shows the dissolution profile from a delivery device in disk form.

Male Erectile Dysfunction:

Apomorphine has been examined by sub-lingual administration in the treatment of male erectile dysfunction (MED). Rapid release is associated with unacceptable side effects (Sublingual administration of apomorphine for erectile dysfunction; Heaton et al. Urology 45 (2) 1995). The hydrogel polymer can be used to slowly release 2 to 5 mg of apomorphine over a suitable time period (FIG. 6—in vitro release).

Apomorphine in vivo Release 1.1 mm thick inserts containing 5, 10 and 20 mg of apomorphine were tested for drug release in six subjects. The levels of drug observed in plasma was 0.2 to 0.8 ng/ml for five of the subjects and reached 5 ng/ml for one subject after administering an insert containing 20 mg of apomorphine.

The used inserts were analysed for residual drug. The data is shown in Table 4A below.

TABLE 4A

| Subject No. | Drug in Insert (mg) | Drug Released (mg) |
|---|---|---|
| 1 | 5 | 0.79 |
| 1 | 10 | 2.30 |
| 1 | 20 | 7.36 |
| 2 | 20 | 1.79 |
| 3 | 90 | 2.58 |
| 4 | 20 | 1.82 |
| 5 | 20 | 1.59 |
| 6 | 20 | 2.15 |
| 2–6 | 5 | 0.08–0.48 |
| 2–6 | 10 | 0.01–0.91 |

Inserts were prepared of thickness 0.6 mm and the release profile in-vitro compared with those of the 1.1 mm thick inserts. The release profile is shown in FIG. 7.

These data show that the release in-vitro is faster from the 0.6 mm slices that the 1.1 mm slices.

A study was carried out in eight subjects. These included two subjects from the previous study and six new subjects. The amount of drug released is shown in Table 4B.

TABLE 4B

| | Apomorphine in-vivo data | | | | |
|---|---|---|---|---|---|
| | | % RELEASE | | | |
| SUBJECT | 10 mg | 18 mg | (am.) | 27 mg | (pm.) |
| 1 | 0.48 | 4.1 | 2.7 | | 4.4 |
| 2 | 25.1 | 7.5 | 6.2 | | 1.3 |
| 3 | 26.0 | 49.2 | 17.7 | | 29.6 |
| 4 | 3.4 | 19.4 | 1.3 | | 3.0 |
| 5 | 6.4 | 2.64 | 0.0 | | 0.0 |
| 6 | 42.8 | 15.2 | 1.1 | | 6.2 |
| 7 | 30.4 | 26.3 | 24.8 | | 32.6 |
| 8 | 10.9 | 21.5 | 9.9 | | 23.6 |

These data show an increased proportion of drug is released from the thinner slices. The blood levels of drug will be measured and the reasons why the 18 mg releases more than the 27 mg will be investigated. Release of between 2 and 9 mg would be expected to give useful blood levels of drug.

ii) Diazepam

This benzodiazepine is administered by the rectal route, using low volume enemas, in the treatment of epileptic seizures. Although rapid and effective the treatment is socially unacceptable and many patients do not receive satisfactory control of their seizures.

Prevention of Seizures:

It is proposed that by delivering diazepam via the buccal route a more rapid onset of action may be achieved compared to the oral route. The patient could self administer the insert discreetly when the signs of an impending seizure are experienced.

Alleviation of Seizures:

If a seizure develops too rapidly for self administration then placing a polymer insert against the gum is much more acceptable for someone else to carry out compared to administering a rectal solution. The polymer insert would be positioned outside the teeth which will be much more practical and safer than attempting to administer a sublingual fast dissolving formulation.

Sedation:

Benzodiazepines such as midazolam and lorazepam are used as sedatives during premedication of procedures such as endoscopy and intubation. A unit which would allow treatment to be terminated after completion of the produce would be preferable to one which persisted (such as an oral tablet or intravenous injection).

(b) Analgesics i) Fentanyl

Peri-operative Pain:

The administration of fentanyl for peri-operative pain via the oral mucosa has proven clinically interesting. A lollipop formulation which can be broken up with the teeth was described in Scrip No.2287, Nov. 25, 1997. However, the lollipop formulation can be broken up into small pieces by crunching with the teeth thus allowing rapid drug release. The potency of fentanyl is such that the risk of overdose is unacceptably high. The polymer is very tough and cannot be easily broken up, even when fully swollen. If the polymer is swallowed the slow release and limited absorption of fentanyl through the gut wall means that there is no risk of overdose.

Breakthrough Pain:

An oral transmucosal (OTM) formulation of fentanyl in a discrete product which does not interfere with speech or oral liquids would be useful as a 'top up' opiate medication.

ii) Buprenorphine

The sub-lingual form of buprenorphine is very effective. However, the abuse potential is such that the product is specially controlled. Slow release OTM systems will be more difficult to extract the drug from and will therefore be less prone to abuse. Other potent molecules such as hydromorphone, oxycodone and dihydrocodeine may be of interest. If the buccal delivery system is swallowed the release rate will be very slow and the low amount of drug absorbed will limit the risk of abuse.

(c)Hormone Replacement Therapy i) Testosterone

Hypogonadism:

It is estimated that there are three–four million men in the US who are hypogondal due to surgery, illness or other causes. There may also be a case for hormone replacement therapy following what is increasingly recognised as male menopause. The current treatment is testosterone either by injection or transdermal patch. The patch has not been nearly as successful as originally anticipated because of the site of application (scrotum) in one form and adhesive problems causing irritation in another (BNF 35th Edition, March 1998).

The use of testosterone supplements in women is also a growing area of interest.

(d)Peptide Molecules

Many of the increasing numbers of peptide molecules generated by biotechnology cannot be delivered by conventional oral dose forms because they are destroyed by the gastrointestinal tract.

Buccal delivery of the nonapetide oxytocin has been achieved in the past (Syntocinon, Sandoz; Martindale 29th Edition, p1147) so there is every reason to expect similar peptides, or even larger molecular weight molecules to be successfully administrated by the oral transmucosal route.

There are limitations on what can be loaded into the hydrogel polymer, in terms of the molecular weight, solubility and ionisation state of the peptide, but some candidates are:

Antidiuretics—e.g. Vasopressin, Desmopressin

Oxytocic Hormones—e.g. Oxytocin, Carbetocin

Growth Hormone Inhibitors—e.g. Ocreotide

Model Peptides

By adjusting the equilibrium solvent uptake (swelling factor) of the polymers a range of model compounds have successfully been loaded into the polymer (see Table 4C).

TABLE 4C

| PEPTIDE | MOLECULAR WT | E.S.U. % | | | |
| --- | --- | --- | --- | --- | --- |
| | | 280 | 490 | 733 | 1120 |
| Melanostatin | 293 | + | + | + | + |
| Lysozyme | 12,000 | − | +/− | + | + |
| Myoglobin | 17,000 | − | − | + | + |
| Bovine Serum Albumin | 60,000 | − | − | +/− | + |

+ = Good uptake
− = no uptake

The release of lysozyme from a polymer with an ESU of 733% is shown in FIG. 8.

Polyurethane polymer was made of polyethylene glycol (molecular weight 20,000), 1,2,6-hexanetriol, and dicyclohexylmethane-4,4'-diisocyanate (Desmodur-W) using a molar ratio of 1:1.2:2.8. The polymer was sliced to a thickness of 0.6 mm. The slices were washed once in an excess volume of 1% W/W disodium dihydrogen ethylenediaminetetra-acetate dihydrate (EDTA), and once in an excess volume of 50% w/w methanol. The temperature was kept at 25° C. and each washing step lasted over 15 hours to ensure the hydrogel was fully swollen and washed thoroughly. After drying under vacuum, the units were stored in a freezer until further use. The swelling factor of this polymer was determined to be 733% (i.e. the hydrogel takes up 7.33 times its own weight in water).

Lysozyme was dissolved in a 20 mM phosphate buffer pH 7.4. Twenty polymer slices (3.38 g) were incubated with 24.79 g solution containing 200.0 mg of lysozyme. The slices were left overnight to soak up the solution. After loading, the slices were blotted dry with tissue paper and ten slices were dried under vacuum. The remaining ten slices were used to determine the protein uptake, by incubating in 10.0 ml of demineralised water for 24 hours, and determining the protein content of this solution using a bicinchoninic acid (BCA) protein assay. It was found that the polymer had absorbed 51.9 mg lysozyme (51.9% of added protein).

To determine the release profile of lysozyme from dried slices, five slices (0.86 g) were placed in a bottle and 30 ml of demineralised water added. Samples were taken regularly and analysed for protein using the BCA assay. A total of 22.9 mg (88.4%) was released after 24 hours.

FIG. 8 shows the release profile of lysozyme over the 21-hour period.

e) Locally Acting Drugs

In addition to the polymer being used to deliver drugs to the systemic circulation the controlled release of locally-acting drugs can be usefully achieved.

Oral Anti-fungal:

Oral candidiasis is a recurrent problem in immunocompromised patients. This includes patients who have been treated for cancer (particularly of the head and neck), as well as patients with AIDS or and other diseases or treatments which compromise the immune system.

Treatment with mouthwashes has been shown to be ineffective. Oral anti-fungal agents, such as Pfizer's Diflucan, are effective but costly. Moreover, they treat systemically what is essentially a local infection. Antifungals can be incorporated in the polymer body.

Inhaled steroids in asthma therapy predispose the user to mouth infection with candida. Oral gels and solutions are used already (Jannsen's Daktarin oral gel, and Squibb's Nystatin oral suspension). The ability to maintain a concentration of an anti-infective in the mouth for a prolonged period is advantageous. This may be an antibiotic or an antiseptic.

Mucositis:

Mucositis is a painful inflammation of the oromucosal tissue generally associated with radiation therapy, particularly to the head and neck. This may be caused by the radiation itself but it is nearly always accompanied by infection from bacterial and fungal agents. The Beatson Oncology Centre in Glasgow has developed a three-drug combination which they provide to their patients for both treatment and prophylaxis following head and neck radiation therapy (R. P. Symonds et al. British Journal of Cancer 74 (1996) p312–317). The product is in the form of a lozenge that dissolves in the mouth but the lozenge lasts for only 15 minutes in its present format. Despite this, encouraging results have been achieved from a placebo controlled clinical trial.

As in the case of mouthwashes to treat candidiasis, the Beatson product does not stay in the oral cavity for a significant period of time. As a result, the patient must take repeat doses and, even if he takes them, the product is often not effective.

Two drugs colistin sulphate and tobramycin sulphate were incorporated in the hydrogel polymer.

By using a sustained-release delivery device according to the present invention, the drug remains in the mouth in sufficient concentration to cure the infection. The antifungal amphotericin was coated on the outside of the device to release quickly and thus allow adhesion to the mucous membrane. There is also the possibility of prophylactic use of such a product. The in-vitro release profiles for tobramycin in a model for the buccal cavity are shown in FIGS. 7 and 8. The drug was assayed using double dilution determination of the minimum inhibitory concentration (MIC) and by HPLC using the Dionex electrochemical detection system. The procedure is described in detail in Example 5.

EXAMPLE 5

In-vitro model to mimic local oral release from an antibiotic buccal hydrogel insert A buccal hydrogel polymer insert containing Tobramycin for serious oral infection was investigated. This drug is not absorbed from the GI tract. The polymer releases the drug into the mouth using the available moisture to swell the polymer and dissolve the drug. Conventional dissolution uses an excess of media which does not equate with the conditions which the device will encounter in the mouth. We simultaneously demonstrated the chemical release of tobramycin using a dissolution model and examined its microbiological activity.

Oral Dissolution Model:

Six cells were sterilised by autoclaving and then connected to a Duran bottle of sterile water. The flow of water into the cell was controlled by a peristaltic pump (Watson Marlow, Falmouth, UK) to a rate of 0.5 ml/minute. Two different dosage forms (5.8 and 10.5 mg tobramycin) as 9.2 mm discs of thickness 1.7 mm and 130 mg weight were tested by placing directly under the inflow tube and media allowed to flow slowly across them.

The dissolution cells were kept at an angle of about 10 degrees to the horizontal to allow flow away from the test units and towards the outflow tube where it was either run to waste or sampled for test. Samples of 2 ml were collected at various timepoints up to 3 hours and divided for chemical (HPLC) and microbiological assay.

Chemical and Microbiological Assay:

Tobramycin chemical analysis was carried out using a Dionex HPLC method. The microbiological assay was carried out by double diluting the eluted fractions with broth. These were then spiked with a known number of microorganisms and incubated. The last tube without growth was then noted. By carrying this out in parallel against a series of prepared standards the inhibitory concentration could be derived.

In-vitro Model Chemical Dissolution and Microbiological Activity:

Table 4 shows the chemical release profiles for Tobramycin from the hydrogel. The method shows good reproducibility between cells and controlled release is maintained for 3 hours in the system. This equates to the maximum retention time the device will be used in the patient. Table 5 shows the microbiological concentrations derived. Excellent agreement is seen between HPLC and microbiological techniques. The results are also shown in FIGS. 9 and 10.

TABLE 5A

Chemical Dissolution of Tobramycin

| Time | 5 mg Dose (mcg/ml) | | | 10 mg Dose (mcg/ml) | | |
|---|---|---|---|---|---|---|
| (hrs) | 1 | 2 | 3 | 1 | 2 | 3 |
| 0.25 | 35.5 | 26.7 | 33.4 | 105.6 | 85.3 | 64.4 |
| 1 | 23.7 | 17.7 | 24.0 | 65.4 | 44.6 | 34.8 |
| 2 | 14.0 | 15.8 | 18.6 | 48.7 | 36.9 | 27.9 |
| 3 | 14.0 | 12.0 | 15.4 | 36.5 | 32.0 | 27.0 |

TABLE 5B

Microbiological Measure of Activity

| Time | 5 mg Dose (mcg/ml) | | | 10 mg Dose (mcg/ml) | | |
|---|---|---|---|---|---|---|
| (hrs) | 1 | 2 | 3 | 1 | 2 | 3 |
| 0.25 | 32 | 32 | 36 | 64 | 64 | 64 |
| 1 | 32 | 16 | 36 | 64 | 32 | 32 |
| 2 | 16 | 16 | 18 | 32 | 32 | 16 |
| 3 | 16 | 16 | 18 | 32 | 32 | 16 |

EXAMPLE 6

(1) Method of Achieving Useful Drug Loading

Hydrogel inserts were loaded with colistin sulphate and tobramycin. It was discovered that by including low molecular weight compounds such as sodium chloride, potassium chloride, sodium saccharin and benzoic acid the uptake of the drugs into the polymer could be increased dramatically. These data are shown in Table 6A.

TABLE 6A

| Co-Solute Concentration 5% | Colistin Sulphate | | Tobramycin | |
|---|---|---|---|---|
| | Drug/Polymer (mg g$^{-1}$) | Drug Uptake (mg) | Drug/Polymer (mg g$^{-1}$) | Drug Uptake (mg) |
| Without Co-Solute | 0.125 | 1.8 | 0.125 | 22.0 |
| Sodium Chloride | 0.125 | 17.6 | — | — |
| Potassium Chloride | 0.34 | 15.1 | — | — |
| Sodium Saccharin | 0.125 | 6.0 | 0.125 | 20.9 |
| Sodium Benzoate | 0.125 | 3.7 | 0.125 | — |
| Phenyl Benzoate | 0.125 | 10.2 | 0.125 | 24.2 |
| Benzoic Acid | 0.125 | 25.5 | 0.125 | 26.5 |
| Mannitol | 0.125 | 8.1 | — | — |
| Sucrose | 0.125 | 9.0 | — | — |

(2) In-vivo Release Data

Hydrogel inserts of different thickness were loaded with colistin sulphate and tobramycin in the presence of benzoic acid co-solute. The release of the two drugs was examined in four healthy subjects. The insert was placed against the buccal mucosa in the upper gingival tissue. Eating and smoking was not permitted during the study, drinking of tea, coffee or soft drinks was allowed. The release data are shown in Table 6B.

TABLE 6B

| | Mean Amount of Drug Released at time points shown (%) | | | |
|---|---|---|---|---|
| Thickness | 1 Hour | | 3 Hours | |
| (mm) | CS | T | CS | T |
| 0.4 | 48.8 | 71.2 | 98.6 | >99 |
| 0.6 | 32.4 | 63.6 | 92.8 | 98.6 |
| 0.8 | 26.7 | 41.8 | 83.4 | 88.7 |
| 1.1 | — | — | 57.9 | 80.8 |

CS = Colistin Sulphate
T = Tobramycin initial

These data show that the insert can be used to deliver these two drugs to the local oropharynx region.

(3) Demonstration of Microbiological Activity

Chemical analysis of colistin sulphate and tobramycin showed that the level of each drug was sufficient to achieve the minimum inhibitory concentration (MIC) value. Microbiological testing in-vitro showed that each of the drugs was microbiologically active when examined alone. A microbiological assay was developed to examine the efficacy of the colistin sulphate and tobramycin when loaded and released from the polymer at the same time. organisms were selected which were sensitive to only one of the antibiotics. Table 6C shows that the activity of each of the antibiotics is not reduced by the presence of the other.

TABLE 6C

| Test Organism | Drug(s) | MIC |
|---|---|---|
| A.Xylosoxidans | Coliston | 8 $\mu$ gml$^{-1}$ |
| A.Xylosoxidans | Tobramycin | >256 $\mu$ gml$^{-1}$ |
| S.Aureus | Coliston | >32 $\mu$ gml$^{-1}$ |
| S.Aureus | Tobramycin | 4 $\mu$ gml$^{-1}$ |

TABLE 6C-continued

| Test Organism | Drug(s) | MIC |
|---|---|---|
| A.Xylosoxidans | Colistin/Tobramycin | 8/64 $\mu$ gml$^{-1}$ |
| S.Aureus | Colistin/Tobramycin | 8/4 $\mu$ gml$^{-1}$ |

EXAMPLE 7

Application of Coating

Amphotericin is a highly insoluble drug and would not be released from the polymer. It is, therefore, desirable to coat the drug onto the surface of the polymer. It is desirable that this release is rapid to allow aqueous fluid to penetrate the polymer and initiate the release of the drugs loaded into the polymer core. A solvent coating was applied by spray coating. The amount of amphotericin in the coating was assayed. The level of drug achieved is shown in Table 7.

TABLE 7

| Coating Time (mins) | Amphotericin (mg) |
|---|---|
| 30 | 0.1 |
| 45 | 0.5 |
| 90 | 2.2 |
| 120 | 3.4 |
| 150 | 4.5 |
| 180 | 5.1 |
| 240 | 7.5 |

Other compounds could be applied in a similar manner providing they were stable under the elevated temperature conditions required for film coating.

Compounds would be selected which were not suitable for aqueous dissolution release or for which an immediate release was desirable. The same compound might be both coated onto the surface and incorporated in the polymer. Examples of applicable compounds include clotrimazole, nystatin, testosterone, apomorphine and those listed in the description herein.

What is claimed is:

1. An autoadhesive oral transmucosal delivery device which comprises;
    a body formed of a hydrogel capable of absorbing water to achieve a water-content whereat the device autoadheres to an oral mucosal surface;
    the hydrogel body being formed of a cross-linked polyurethane;
    the hydrogel body comprising a pharmaceutically active agent which is released while the body is adhered to the mucosal surface;
    the hydrogel body subsequently detaching from the mucosal surface.

2. A device according to claim 1 wherein the hydrogel contains less than 2 wt % water.

3. A device according to claim 2 wherein the hydrogel contains less than 1 wt % water.

4. A device according to any preceding claim wherein said autoadhering water-content is below 50 wt %.

5. A device according to any preceding claim wherein said autoadhering water-content is above 25 wt %.

6. A device according to any preceding claim wherein said autoadhering water-content is in the range 35 to 45 wt %.

7. A device according to any preceding claim having a rate of water uptake sufficient to allow the device to autoadhere to mucosal membranes in less than 15 minutes.

8. A device according to any preceding claim having an adherence period in the range 2 to 3 hours before the device detaches.

9. A device according to any preceding claim in the form of a strip of smallest dimension in the range 5 to 15 mm and longest dimension in the range 10 to 25 mm.

10. A device according to any preceding claim having a thickness in the range 0.5 to 5 mm.

11. A device according to any preceding claim which further comprises a co-solute effective to increase the maximum loading of active agent in the hydrogel.

12. A device according to claim 11 wherein the co-solute is selected from sodium chloride, potassium chloride, sodium saccharin and benzoic acid.

13. A device according to any preceding claim which comprises a mixture of at least two active agents.

14. A device according to any preceding claim wherein the active agent is a protein.

15. A device according to any of claims 1 to 13 wherein the active agent is apomorphine.

16. A device according to any of claims 1 to 13 wherein the active agent is benzodiazepine.

17. A device according to any of claims 1 to 13 wherein the active agent is an antimicrobial.

18. A device according to any preceding claim having a coating comprising a further pharmaceutically active agent.

19. A device according to claim 18 wherein the further active agent compound in the coating is apomorphine.

* * * * *